United States Patent
Siverling et al.

(10) Patent No.: US 6,945,113 B2
(45) Date of Patent: Sep. 20, 2005

(54) END-TO-END ULTRASONIC INSPECTION OF TUBULAR GOODS

(76) Inventors: David E. Siverling, Four Points Mgmt., Grand Galleria, Suite 220, 43-46 Norre Gade, St. Thomas (VG), 00802; Doug R. Lester, 1102 Aberdeen, Pasadena, TX (US) 77502; Bill McWhorter, 16937 Leonard Rd., Houston, TX (US) 77049

( * ) Notice: Subject to any disclaimer, the term of this patent is extended or adjusted under 35 U.S.C. 154(b) by 70 days.

(21) Appl. No.: 10/633,024

(22) Filed: Aug. 1, 2003

(65) Prior Publication Data

US 2004/0020298 A1 Feb. 5, 2004

Related U.S. Application Data

(60) Provisional application No. 60/400,648, filed on Aug. 2, 2002.

(51) Int. Cl.$^7$ .............................................. G01N 29/10
(52) U.S. Cl. .......................................... 73/622; 73/638
(58) Field of Search ........................... 73/622, 623, 602, 73/644

(56) References Cited

U.S. PATENT DOCUMENTS

| | | | |
|---|---|---|---|
| 3,921,440 A | * 11/1975 | Toth | 73/622 |
| 3,981,184 A | * 9/1976 | Matay | 73/609 |
| 4,018,082 A | 4/1977 | Manoliu et al. | 73/67.5 R |
| 4,106,347 A | 8/1978 | DeKerlegand | 73/622 |
| 4,586,379 A | * 5/1986 | Burkhardt, Jr. | 73/622 |
| 4,700,572 A | * 10/1987 | Senba et al. | 73/622 |
| 4,760,737 A | * 8/1988 | Kupperman | 73/622 |
| 5,007,291 A | 4/1991 | Walters et al. | 73/640 |
| 5,123,281 A | 6/1992 | Cox et al. | 73/644 |
| 5,431,054 A | * 7/1995 | Reeves et al. | 73/612 |
| 5,585,565 A | * 12/1996 | Glascock et al. | 73/644 |
| 5,600,069 A | 2/1997 | Girndt et al. | 73/622 |
| 5,747,693 A | * 5/1998 | Abbate et al. | 73/622 |
| 5,969,255 A | 10/1999 | McLean | 73/622 |
| 6,578,422 B2 | * 6/2003 | Lam et al. | 73/622 |
| 6,622,561 B2 | * 9/2003 | Lam et al. | 73/622 |

OTHER PUBLICATIONS

Terrance R. Banach, Ultrasonic Test Coverage—Planned Versus Actual, Tube & Pipe Technology, pp. 45–52, Mar./Apr. 1995.

* cited by examiner

*Primary Examiner*—Hezron Williams
*Assistant Examiner*—Rose M. Miller

(57) ABSTRACT

The present technique provides a system and method for ultrasonically testing a tubular good along the entire axial length of the material using a single ultrasonic test assembly. The ultrasonic test assembly has an ultrasonic tubular inspection unit movable lengthwise along a tubular and an end-crossing extension mechanism adapted to facilitate end inspection of the tubular.

20 Claims, 7 Drawing Sheets

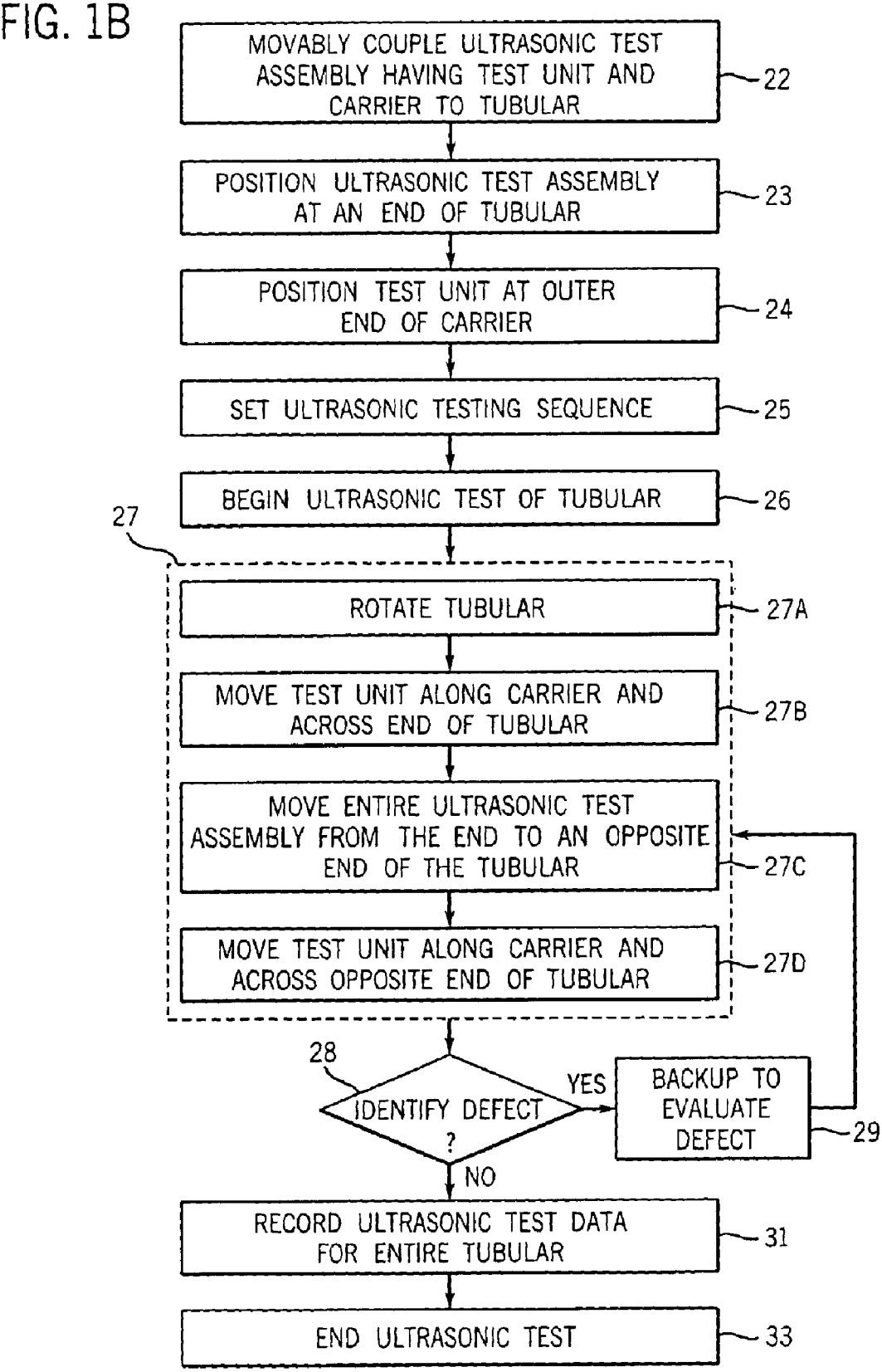

END-TO-END ULTRASONIC INSPECTION OF TUBULAR GOODS

PRIORITY

The present application claims priority to provisional patent application Ser. No. 60/400,648, filed on Aug. 2, 2002.

FIELD OF THE INVENTION

The present technique relates generally to tubular inspection systems and, more particularly, to ultrasonic tubular inspection techniques for various tubular goods, such as oil country tubular goods (OCTG). The present technique provides a system and method for ultrasonically testing a tubular good completely through end and body regions of the tubular good to provide a complete ultrasonic test of the tubular good.

BACKGROUND OF THE INVENTION

Tubular goods are used in a variety of industrial applications, which may be particularly sensitive to internal defects. For example, a particular tubular good may have internal-external thickness variations, hairline fractures, seams, and various other longitudinally-oriented, transversely-oriented, and obliquely-oriented defects, which may be undetectable by alternative inspection techniques. These defects may arise during the initial manufacturing process, the subsequent processing or transportation, or they may occur as service-induced defects. In many industrial applications, the foregoing defects may lead to environmental damage, bodily injury, equipment damage and downtime, and loss of the associated product, such as hydrocarbon reserves.

Ultrasonic testing has been found to be particularly useful in detecting the foregoing defects, and in certain instances, ultrasonic testing provides the only detection mechanism for such defects. A variety of ultrasonic testing systems currently exist for testing tubular goods following manufacture and other processing stages. Each of these ultrasonic testing systems performs an ultrasonic examination in a helical scanning pattern about the surface of the tubular good. In fluid immersion systems, the tubular good is moved rotationally and longitudinally through a fluid bath, where a number of ultrasonic transducers reside. Although the fluid medium provides relatively low signal degradation from the ultrasonic transducers, these fluid immersion systems are cumbersome and difficult to use in pinpointing defects due to the size and momentum of the tubular goods. In rotating head systems, an assembly of ultrasonic transducers is rotated at high speeds about a tubular good, which is moved longitudinally through the rotating head assembly. Again, the size and momentum of the tubular good complicates the pinpointing of defects within the tubular good.

In other systems, the ultrasonic transducers are mounted in a contoured solid material, such as polystyrene or Lucite, which is moved along the rotating tubular good. In a different application, the ultrasonic transducers may be mounted in a rubber or polystyrene wheel. Both of these systems have a relatively lower sensitivity due to the use of an additional solid interface between the tubular good and the ultrasonic transducers. Moreover, the solids may have defects, such as scratches, which further reduce the ultrasonic sensitivity. These solid-interface systems also have other drawbacks, such as the inability to focus the ultrasonic beams, the relatively narrow inspection width of the rubber wheel system, and the consumability of the polystyrene shoe system.

The foregoing ultrasonic testing systems generally do not test ends of the tubular good, but rather a separate end-testing unit is used to perform an inspection at each end of the tubular good. Special End-Area-Testing units are necessary to complete the testing of the tubular good, because the foregoing ultrasonic testing systems are incapable of traveling fully across the tubular good from end-to-end. Special End-Area inspection units may use ultrasonic means, but more typically employ wet or dry magnetic particle methods. The magnetic particle inspection methods do not provide for a hard copy record of the test, and is less sensitive to internal defects than ultrasonic tests. For example, an ultrasonic testing system having a length of 18 inches is incapable of fully testing the outer 18 inches at each end of the tubular good.

Accordingly, a technique is needed for ultrasonically testing a tubular good from end-to-end using a single ultrasonic testing assembly. A technique is also needed for ultrasonically testing the tubular good through a fluid interface with the tubular good, which is rotated while the ultrasonic testing assembly is moved along the tubular good.

SUMMARY OF THE INVENTION

The present technique provides a system and method for ultrasonically testing a tubular good along the entire axial length of the material using a single ultrasonic test assembly. The ultrasonic test assembly has an ultrasonic test unit movably disposed in a carrier, which may be movably coupled to the tubular good. Ultrasonic transducers are mountable in the ultrasonic test unit, such that ultrasound waves are transmittable through an interface, such as a liquid or solid interface, between the tubular good and the ultrasonic transducers. The ultrasonic test unit and/or the carrier also may have a removable interface structure, which serves as a replaceable wear surface. A variety of positioning and control system also may be provided to perform an ultrasonic test of the tubular good. For example, the positioning and control system may have drive assemblies for rotating the tubular good, for moving the ultrasonic test assembly along the tubular, and for moving the ultrasonic test unit along the carrier. In operation, the ultrasonic test assembly is disposed at an end of the tubular good and the ultrasonic test unit is disposed at an outer region of the carrier. The ultrasonic test unit then moves along the carrier and across the end for ultrasonically testing the end. The entire ultrasonic test assembly then moves along the tubular good to the opposite end for ultrasonically testing the central body region of the tubular good. The ultrasonic test unit then moves along the carrier and across the opposite end for ultrasonically testing the opposite end.

BRIEF DESCRIPTION OF THE DRAWINGS

Exemplary embodiments will hereafter be described with reference to the accompanying drawings, wherein like reference numerals denote like elements, and:

FIG. 1B is a flow chart illustrating an exemplary end-to-end ultrasonic test process using the system of FIG. 1A;

DETAILED DESCRIPTION OF SPECIFIC EMBODIMENTS

As described in detail below, a system and method is provided for ultrasonically testing a tubular good using a movable ultrasonic test assembly. In one embodiment, the movable ultrasonic test assembly is top-mounted to the tubular good, such that a fluid interface is formed between the tubular good and ultrasonic transducers disposed in the movable ultrasonic test assembly. In another embodiment, the movable ultrasonic test assembly comprises an ultrasonic test unit movably disposed in a movable carrier unit, which may be movably coupled to the tubular good. The foregoing assembly facilitates complete end-to-end testing of the tubular good by movably extending the ultrasonic test unit beyond the ends of the tubular goods, such that the ultrasonic test unit can ultrasonically test the tubular ends. As with the former embodiment, the latter end-to-end testing assembly may have a fluid interface with the tubular good to optimize ultrasonic testing. However, the end-to-end testing assembly may comprise any suitable ultrasonic test assembly and tubular interface, such as a solid or solid/liquid interface between the tubular good and ultrasonic transducers disposed in the ultrasonic test unit.

In either of the foregoing embodiments, a fluid interface provides relatively strong signal transmission to the tubular good, while the movability of the ultrasonic test assembly avoids the cumbersome movement of large tubular goods. Accordingly, the movability of the ultrasonic test assembly allows rapid return of the ultrasonic transducers to a potential flaw, rather than requiring movement of the tubular good back to the flaw. The ultrasonic transducers may be disposed in a variety of normal-flaw-detection, transverse-flaw-detection, longitudinal-flaw-detection, and oblique-flaw-detection orientations in one or multiple directions, such as left/right and clockwise/counterclockwise directions. Moreover, the ultrasonic transducers may have curved lenses, such as spherical or cylindrical lenses, to focus the ultrasound (e.g., more collimated ultrasound) for better detection of defects and less signal degradation due to the curved surface of the tubular good. The movable ultrasonic test assembly of the present technique also may have a removable contact member, which makes the assembly a non-consumable item that endures repeated use by replacing the removable contact member after a degree of wear.

Figure 1A:
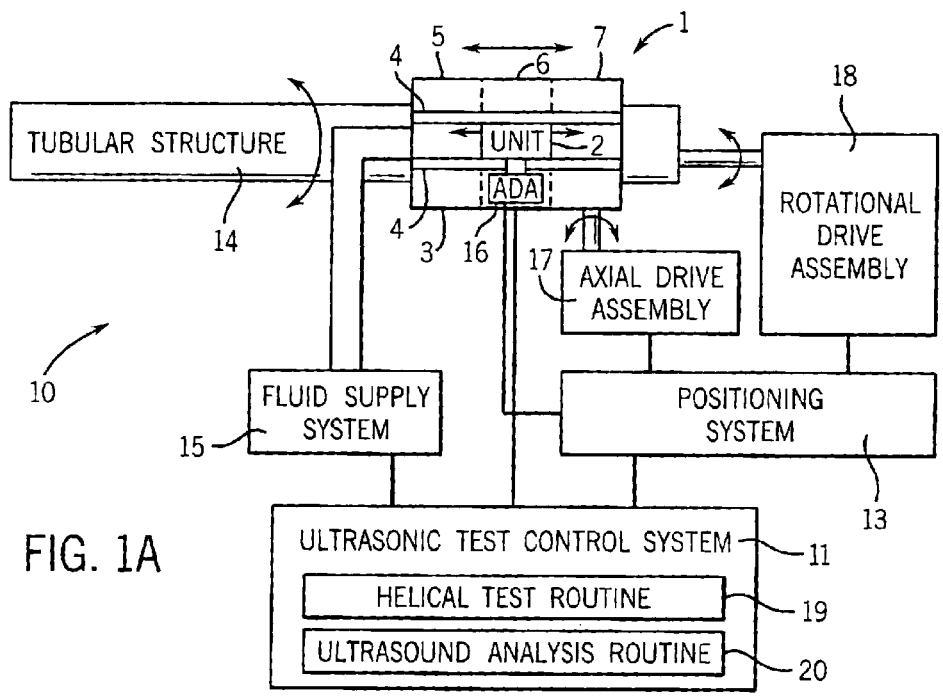
FIG. 1A is a diagram of an exemplary ultrasonic test system of the present technique.

FIG. 1A is a diagram illustrating an exemplary ultrasonic test system 10 for complete end-to-end tubular testing using ultrasound. As illustrated, the system 10 comprises an ultrasonic test assembly 1 having an ultrasonic test unit 2, which is movably disposed in a carrier 3 via a positioning assembly 4. The positioning assembly 4 extends across an outer section or extension 5, a central section 6, and an outer section or extension 7 of the carrier 3. In operation, the positioning assembly 4 moves the ultrasonic test unit 2 across the sections 5, 6, and 7 to facilitate end testing of a tubular good 14. The tubular good 14 may comprise oilfield casing, tubing, drill pipe, line pipe, or a variety of other oilfield or other industrial tubular goods. The ultrasonic test unit 2 is also movable along the length of the tubular good 14 via the carrier 3, which may be movably mounted to the tubular good 14 for an ultrasonic test sequence. Accordingly, the carrier 3 facilitates intermediate testing of the tubular good 14 between the opposite ends 8 and 9. In operation, the ultrasonic test assembly 1 moves the ultrasonic test unit 2 completely across the tubular good 14, including the opposite ends 8 and 9. For example, the carrier 3 may interface the tubular good 14 via the central section 6, such that the outer sections 5 and 7 extend beyond opposite ends 8 and 9 of the tubular good 14 when the carrier 3 is moved to the respective one of the opposite ends 8 and 9. Accordingly, the ultrasonic test unit 2 can ultrasonically test each of the opposite ends 8 and 9 by moving from the central section 6 to the overextended one of the outer sections 5 and 7.

As illustrated, the system 10 also may include a variety of positioning and control assemblies. For example, the ultrasonic test system 10 may include an ultrasonic test control system 11, which may be communicatively coupled to a positioning system 13. If the ultrasonic test assembly 1 has a fluid interface with the tubular good 14, then the ultrasonic test control system 11 also may be coupled to a fluid supply system 15. However, as discussed below, the ultrasonic test assembly 1 may have a solid or solid/fluid interface, rather than an entirely fluid interface between the tubular good 14 and ultrasonic transducers in the unit 2. If included in system 10, the fluid supply system 15 feeds a desired fluid, such as water, to the ultrasonic test assembly 1 to maintain a fluid interface between ultrasonic transducers and a top surface of the tubular good 14.

The positioning system 13 may be communicatively coupled to a variety of motorized drive assemblies, such as an axial drive assembly 16 for longitudinally moving the ultrasonic test unit 2, an axial drive assembly 17 for longitudinally moving the carrier 3, and a rotational drive assembly 18 for rotating the tubular good 14. Accordingly, the positioning system 13 cooperates with the axial drive assembly 16 to move the ultrasonic test unit 2 longitudinally across the sections 5, 6, and 7. The positioning assembly 13 also cooperates with the axial drive assembly 17 to move the carrier 3 longitudinally along the tubular good 14 between the opposite ends 8 and 9. The positioning assembly 13 further cooperates with the rotational drive assembly 18 to rotate the tubular good 14 relative to the ultrasonic test assembly 1. Alternatively, the ultrasonic test assembly 1 may have a longitudinal and rotational drive assembly, which facilitates movement of the test assembly 1 along and around the tubular good 14 to minimize movement of the bulky tubular good 14 during ultrasonic testing.

In operation, the ultrasonic test control system 11 may execute a helical test routine 19 to move the ultrasonic test assembly 1 (e.g., ultrasonic test unit 2 and carrier 3) and rotate the tubular good 14, such that ultrasonic transducers in the assembly 1 traverse the tubular good 14 in a helical test pattern completely across the tubular good 14 from end to end. During an ultrasonic test sequence, the system 10 also may identify, record, and analyze anomalies/defects in the tubular good 14. For example, the ultrasonic test control system 11 may have an ultrasound analysis routine 20 for evaluating ultrasound reflections and identifying defects in the tubular good 14. Any other suitable hardware and software is also within the scope of the present technique.

Figure 1C:
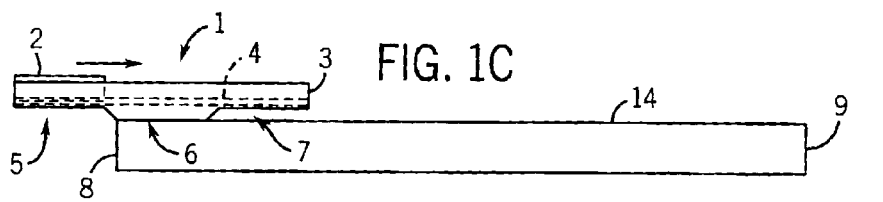
FIGS. 1C–1F are side views of an exemplary ultrasonic test assembly illustrating a complete end-to-end ultrasonic test using the system and process of FIGS. 1A–1B.

FIG. 1B is a flow chart illustrating an exemplary ultrasonic testing process of the present technique. As illustrated, the process 21 proceeds by movably coupling the ultrasonic test assembly 1 having the test unit 2 and the carrier 3 to tubular good 14 (block 22). Although the process 21 may perform an ultrasonic test in any portion of the tubular good 14, the process 21 may be configured to perform an end-to-end test as described below. Accordingly, the process 21 proceeds to position the ultrasonic test assembly 1 at the end 8 of the tubular good 14 (block 23). The process 21 also positions the test unit 2 at an outer end, i.e., outer section 5, of the carrier 3 extending beyond the end 8 (block 24). FIG. 1C illustrates the positioning achieved by blocks 22–24. A user may then select a variety of testing options, program custom testing procedures, and generally setup the system 10 for a desired ultrasonic testing sequence (block 25). The process 21 then begins an ultrasonic test of the tubular good 14 (block 26).

Figure 1D:
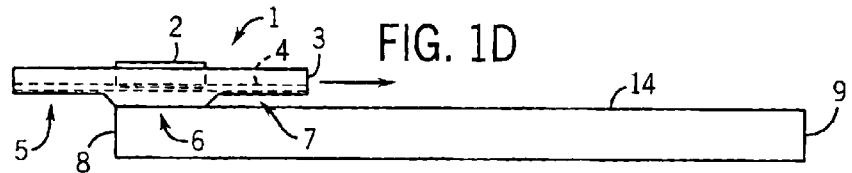
Figure 1E:
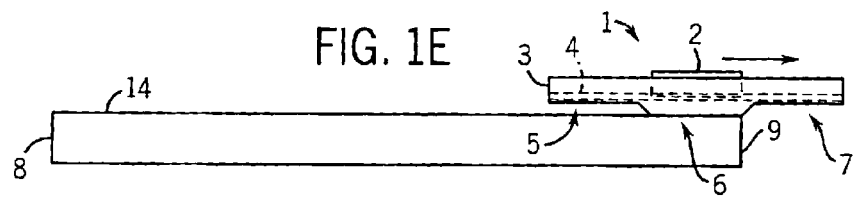
Figure 1F:
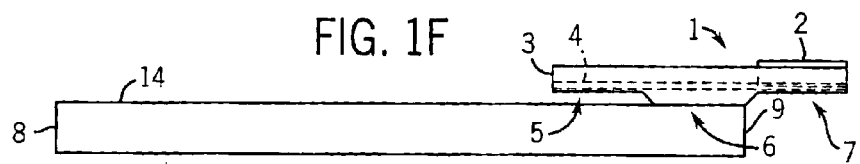

At testing block 27, the process 21 performs a variety of end tests and intermediate tests of the tubular good 14. For example, the process 21 may rotate the tubular good 14 at a desired testing velocity to facilitate helical testing as the ultrasonic test assembly traverses the tubular good 14 (block 27A). At block 27B, the process 21 proceeds by moving the ultrasonic test unit 2 along the carrier 3 and across the end 8 of the tubular good 14 for ultrasonically testing the end 8, as illustrated by FIGS. 1C–1D. Upon reaching the central section 6, the process 21 proceeds to move the entire ultrasonic test assembly 1 along the tubular good 14 to the opposite end 9 via the carrier 3, as illustrated by FIGS. 1D–1E (block 27C). At the opposite end 9, the process 21 continues the ultrasonic testing sequence across the end 9 by moving the ultrasonic test unit 2 along the carrier 3 from the central section 6 to the outer sections 7 overextending the end 9, as illustrated by FIGS. 1E–1F (block 27D).

If the process 21 identifies a defect (or potential defect) at any time during the ultrasonic testing sequence, then the process 21 may backup the test unit 2 to further evaluate the potential defect (block 29). The process 21 then proceeds with the ultrasonic test sequence at block 27. If the process 21 does not identify any defects, then the process 21 proceeds to record the ultrasonic test data for the entire tubular good 14 (block 31). Accordingly, ultrasonic test data may be stored for both ends 8 and 9 and the intermediate region between the opposite ends 8 and 9. The process 21 is then ended at block 33. If additional testing is desired, then a user may repeat the process 21.

As discussed in detail below, the system 10 may utilize any suitable ultrasonic test assembly 1, which may have a liquid interface, a solid interface, or a liquid/solid interface with ultrasonic transducers disposed therein. Moreover, the carrier 3 may provide a liquid interface, a solid interface, or a liquid/solid interface between the ultrasonic test assembly 1 and the tubular good 14. Although a fluid interface provides relatively stronger signal transmission between the ultrasonic transducers and the tubular good 14, the system 10 and ultrasonic test assembly 1 are not intended to be limited to any particular test unit. The present technique may retrofit or generally adapt any suitable test unit into the carrier 3 of the ultrasonic test assembly 1. However, an exemplary embodiment of the ultrasonic test assembly 1 provides a continuous fluid interface 35 between the tubular good 14 and ultrasonic transducers in the test unit 2, as illustrated by FIGS. 1G–1H.

Figure 1G:
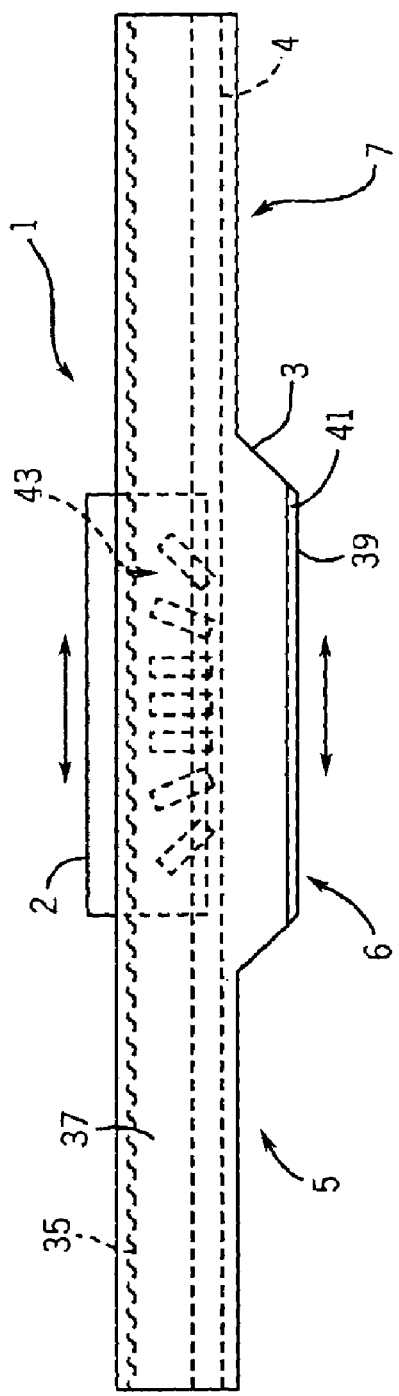
FIG. 1G is a side view of the ultrasonic test assembly having a fluid interface between the tubular good and ultrasonic transducers.
Figure 1H:
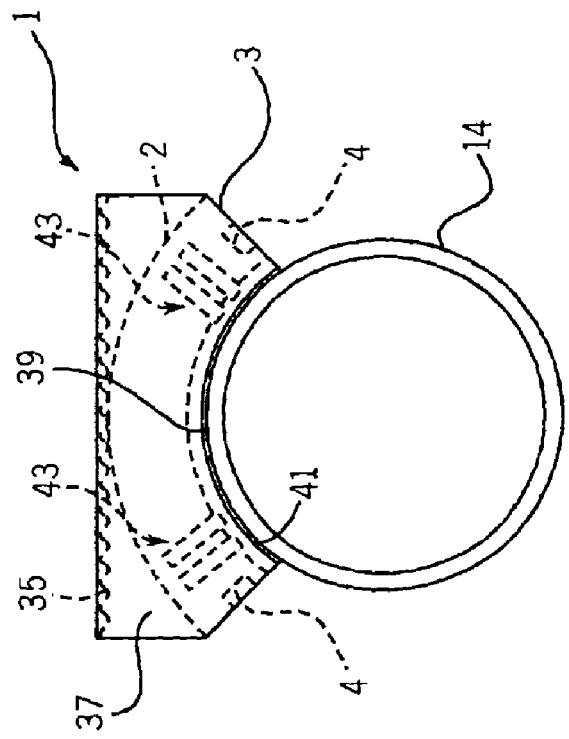
FIG. 1H is an end view of the ultrasonic test assembly of FIG. 1G movably coupled to the tubular good.

FIGS. 1G and 1H are side and end views, respectively, of the ultrasonic test assembly 1 having the continuous fluid interface 35. As illustrated, the carrier 3 has an internal cavity 37 and an open interface 39, which is movable and substantially sealable along the tubular good 14. Accordingly, the internal cavity 37 is filled with the fluid 35 after mounting the carrier 3 to the tubular good 14. It should be noted that the open interface 39 is disposed within the central section 6 of the carrier 3, such that a fluid seal is maintained with the tubular good 14 when the ultrasonic test assembly 1 is positioned at one of the tubular ends 8 or 9. The open interface 39 also may have a removable wear surface 41, such as a low friction material or self-lubricating material, e.g., UHMW, Teflon, or any other suitable long-chain polymer. In operation, the removable wear surface 41 slides along the surface of the tubular good 14 and substantially retains fluid within the internal cavity 37 of the carrier 3. At any time, the removable contact member 150 may be replaced with another removable wear surface 41 to refurbish the ultrasonic test assembly 1 or to accommodate a different ultrasonic test, a different tubular good, or any other testing conditions. The removable wear surface 41 also allows the ultrasonic test assembly 1 to be formed from any desired material, because the tubular good 14 interfaces with the removable wear surface 41 rather than the ultrasonic test assembly 1. For example, the ultrasonic test assembly 1 may comprise aluminum, nylon, nylatride, Delrin, or any other rigid material.

Inside the internal cavity 37 of the carrier 3, the ultrasonic test unit 2 is movable along the positioning assembly 4 within the fluid 35. The positioning assembly 4 may comprise one or more rail structures, male and female sliding structures, or any other suitable linear positioning mechanism. As mentioned above, the ultrasonic test unit 2 may embody any suitable ultrasonic test head having one or more ultrasonic transducers, such as ultrasonic transducers 43. The ultrasonic transducers 43 may be positioned in one or more testing orientations, such as perpendicular angles, longitudinally-oriented angles, transversely-oriented angles, and obliquely-oriented angles to detect perpendicular defects, transverse defects, longitudinal defects, and oblique defects, respectively. Again, the ultrasonic test unit 2 may have a solid, liquid, or solid/liquid interface between the ultrasonic transducers 43 and the fluid 35. In the illustrated embodiment, the ultrasonic transducers 43 are open to the fluid 35 to provide a relatively strong signal transmission and response between the transducers 43 and the tubular good 14.

Figure 2:
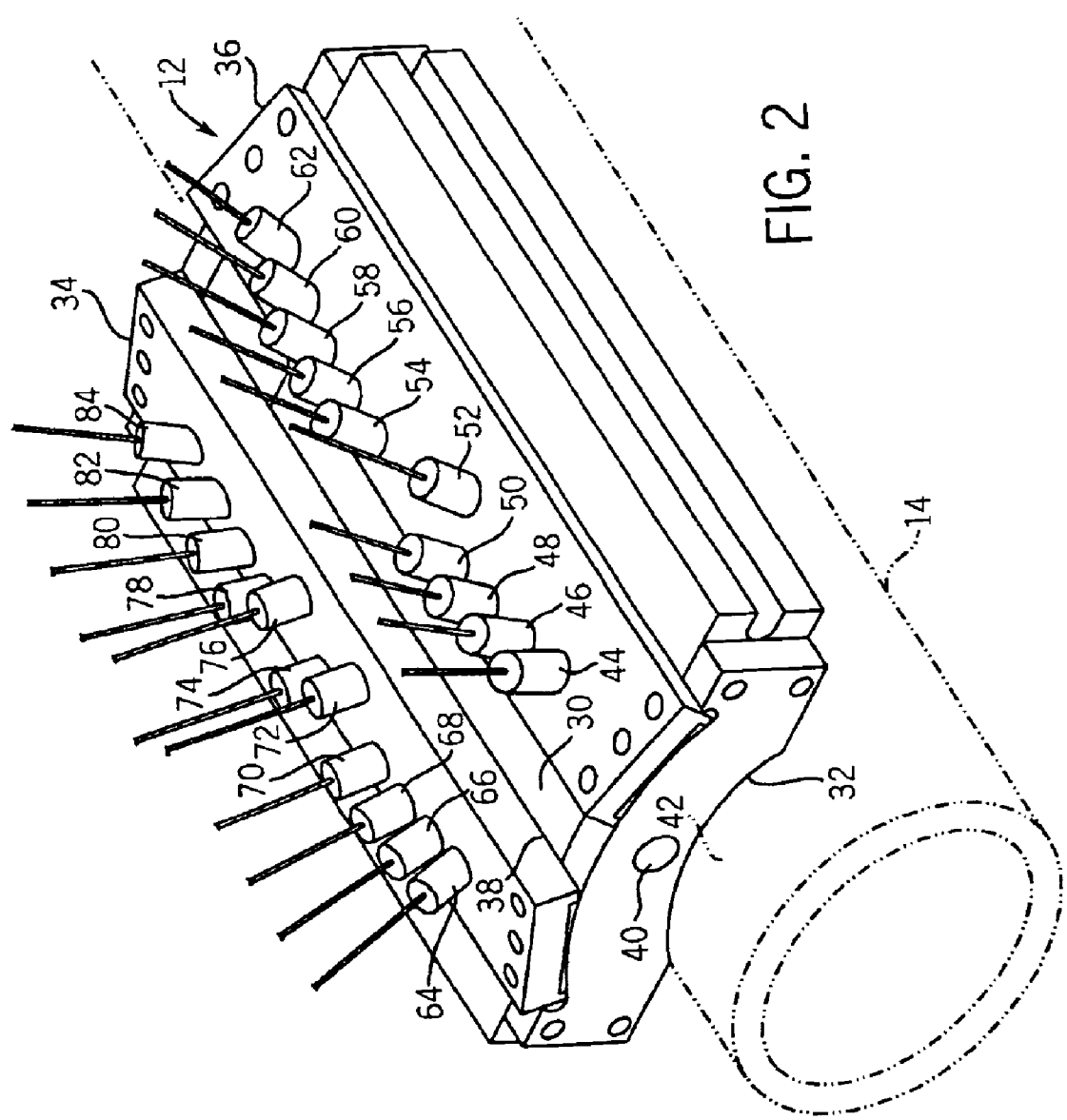
FIG. 2 is a perspective view of an exemplary ultrasonic test assembly of the system illustrated by FIG. 1A.

The ultrasonic test assembly 12 illustrated with reference to FIGS. 2–8 is provided as an exemplary ultrasonic test unit, which may be adapted to operate as the ultrasonic test unit 2 in the ultrasonic test assembly 1 of FIGS. 1A–1H. FIG. 2 is a perspective view of an exemplary embodiment of the ultrasonic test assembly 12 top-mounted to the tubular good 14. As illustrated, the ultrasonic test assembly 12 has a fluid chamber 30 disposed between a mount interface 32 and a pair of transducer mount panels 34 and 36. The illustrated fluid chamber 30 is open at a top opening 38 between the transducer mount panels 34 and 36 and is fillable via a fluid inlet 40. However, the fluid chamber 30 may comprise any suitable fluid retention structure and filling mechanism. For example, the fluid chamber 30 may comprise a pressurized fluid chamber to allow positioning of the ultrasonic test assembly 12 at any position around the tubular good 14. The mount interface 32 is substantially sealable against a top surface 42 of the tubular good 14, such that fluid is substantially retained within the fluid chamber 30 in fluid contact with the top surface 42 and ultrasonic transducers disposed within the transducer mount panels 34 and 36. As illustrated, the transducer mount panels 34 and 36 have ultrasonic transducer units 44–84 disposed in transducer mount receptacles, which may be in transverse, longitudinal, perpendicular, or oblique testing orientations in one or more directions relative to the tubular good 14.

Figure 3:
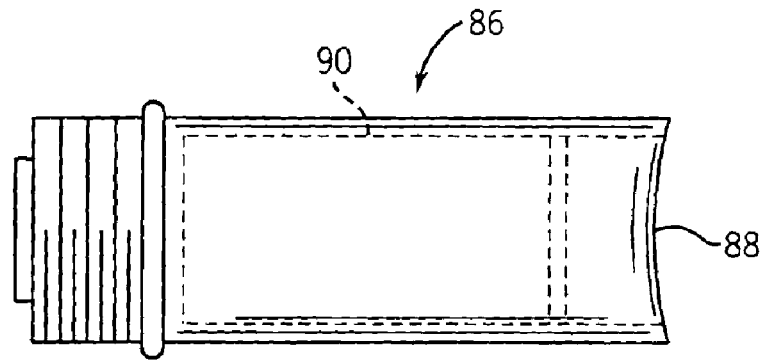
FIG. 3 is a side view of an exemplary ultrasonic transducer unit for the ultrasonic test assembly illustrated by FIG. 2.

Each of the ultrasonic transducer units 44–84 also may comprise a variety of ultrasonic transducer elements, lenses, and circuitry to transmit a desired ultrasonic beam and interpret an ultrasonic echo reflected back from a defect. For example, the ultrasonic transducer units 44–84 may comprise a piezoelectric element and a lens, such as a flat, cylindrical, or spherical lens. The curved lenses accommodate the curved surface of the tubular good 14 to minimize the loss of incident sound energy on the curved surface of the tubular good 14. In operation, the cylindrical lens focuses sound energy to a line and the spherical lens focuses sound energy to a spot. FIG. 3 is a side view of an exemplary line-focused ultrasonic transducer unit 86, which has a cylindrical lens 88 and an internal piezoelectric element 90 for transmitting and receiving ultrasounds. Accordingly, the ultrasonic test assembly 12 of the present technique may use spot-focused or line-focused ultrasonic transducer units to provide more accurate detection of internal defects.

Figure 4:
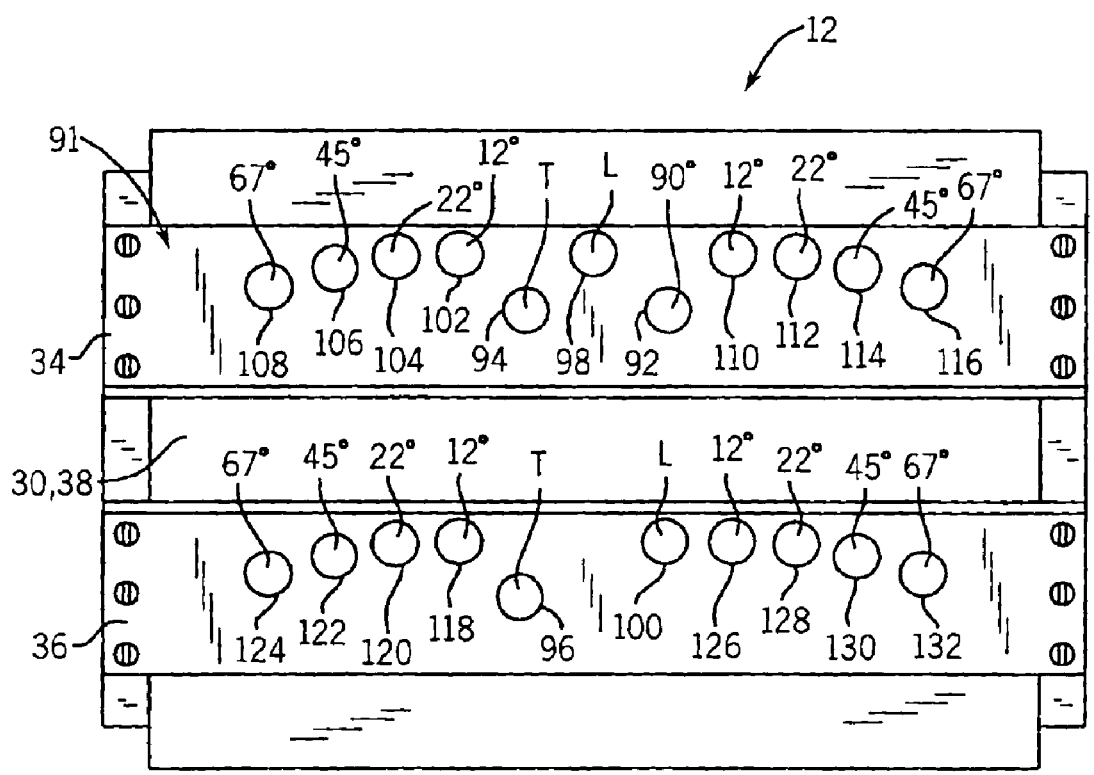
FIG. 4 is top view of the ultrasonic test assembly of FIG. 2 illustrating a plurality of differently oriented receptacles for the ultrasonic transducer unit illustrated by FIG. 3.

The ultrasonic test assembly 12 also may position the ultrasonic transducer units 44–84 in a variety of detection orientations and directions. FIG. 4 is a top view of the ultrasonic test assembly 12 having a plurality of transducer mount receptacles 91 disposed in the transducer mount panels 34 and 36. As illustrated, the transducer mount receptacles 91 are disposed in perpendicular angles, longitudinally-oriented angles, transversely-oriented angles, and obliquely-oriented angles to detect perpendicular defects, transverse defects, longitudinal defects, and oblique defects, respectively. The foregoing defects are detected by positioning the ultrasonic transducer units 44–84 at an incident angle in the fluid within the fluid chamber 30, such that the ultrasonic transducer units 44–84 generate a shear wave mode in the tubular good 14 at, for example, an angle of approximately 45 degrees. For transverse flaw detection, an exemplary incident angle is approximately 17 degrees. The incident angles for longitudinal and oblique flaw detection varies depending on the curve of the tubular good 14. The transducer mount receptacles 91 are also staggered to provide for a complete coverage of the tubular good 14 during the ultrasonic inspection. In this exemplary embodiment, the transducer mount receptacles 91 may be configured for a 30 percent overlap of the mounted ultrasonic transducer units 44–84.

In the illustrated embodiment of FIG. 4, the transducer mount receptacles 91 comprise a normal-detection receptacle 92, transverse-detection receptacles 94 and 96, and longitudinal-detection receptacles 98 and 100. The normal-detection receptacle 92 is oriented normal to the curved surface of the tubular good 14 to direct sound waves perpendicularly into the tubular good 14. These normally-directed sound waves detect wall thickness variations in the tubular good 14. The transverse-detection receptacles 94 and 96 are angled along the axis of the tubular good 14 to direct sound waves from a mounted ultrasonic transducer unit longitudinally along the tubular good 14. These longitudinally directed sound waves detect transverse flaws within the tubular good 14. As noted above, the transverse-detection receptacles 94 and 96 are disposed at an incident angle of 17 degrees. The transverse-detection receptacles 94 and 96 also may be disposed in different directions, such as leftward and rightward directions, relative to the tubular good 14.

The longitudinal-detection receptacles 98 and 100 are angled circumferentially about the tubular good 14 to direct sound waves from a mounted ultrasonic transducer unit around the circumference of the tubular good 14. These circumferentially or transversely directed sound waves detect longitudinal flaws within the tubular good 14. Again, the longitudinal-detection receptacles 98 and 100 may be disposed in different directions, such as clockwise and counterclockwise directions, relative to the tubular good 14. For example, the off-center positioning of the transducer mount panels 34 and 36 may facilitate multi-directional ultrasonic testing in the various testing orientations. The foregoing multi-directional positioning is discussed in further detail below with reference to FIGS. 5 and 6.

If oblique-flaw detection is desired, then a variety of oblique-detection receptacles may be disposed within the ultrasonic test assembly 12. The transducer mount receptacles 91 illustrated by FIG. 4 comprise oblique-detection receptacles 102–116 and 118–132, which are disposed in transducer mount panels 34 and 36, respectively. The oblique-detection receptacles 102, 104, 106, and 108 are obliquely-oriented for detection of oblique-flaws at exemplary angles of 12, 22.5, 45, and 67 degrees in a leftward clockwise direction relative to the tubular good 14. In this same example, the oblique-detection receptacles 110, 112, 114, and 116 are obliquely-oriented for detection of oblique-flaws at exemplary angles of 12, 22.5, 45, and 67 degrees in a rightward clockwise direction relative to the tubular good 14. The oblique-detection receptacles 118, 120, 122, and 124 are obliquely-oriented for detection of oblique-flaws at exemplary angles of 12, 22.5, 45, and 67 degrees in a leftward counterclockwise direction relative to the tubular good 14. The oblique-detection receptacles 126, 128, 130, and 132 are obliquely-oriented for detection of oblique-flaws at exemplary angles of 12, 22.5, 45, and 67 degrees in a rightward counterclockwise direction relative to the tubular good 14. Again, an incident angle is selected to generate an exemplary 45 degree shear wave in the tubular good 14 for each of the foregoing oblique-detection receptacles.

Figure 5:
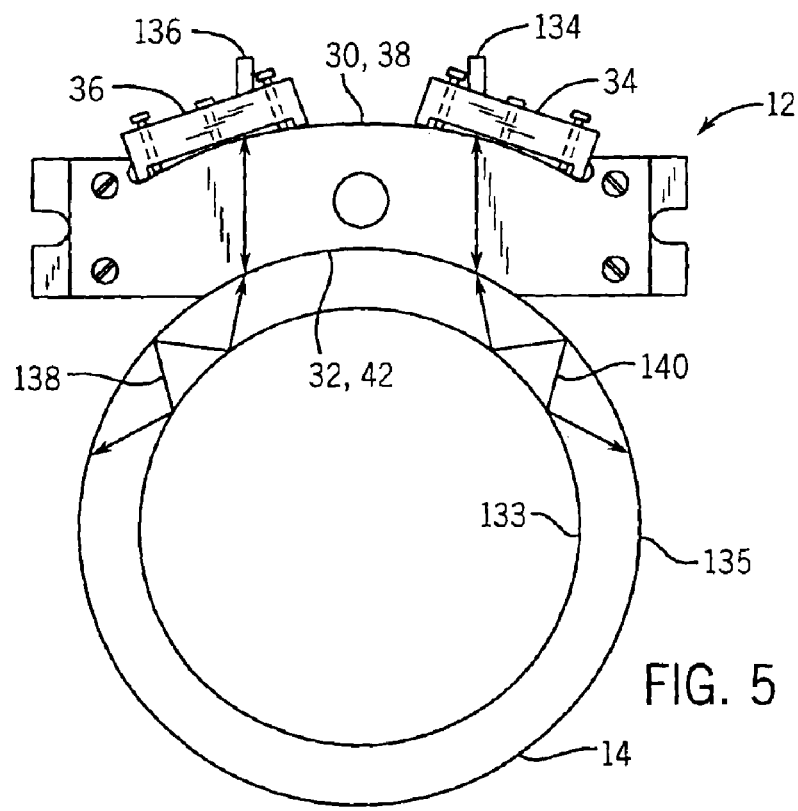
FIG. 5 is an end view of the ultrasonic test assembly of FIG. 2 top-mounted to a tubular illustrating transverse ultrasonic testing in opposite directions around the circumference of the tubular good.
Figure 6:
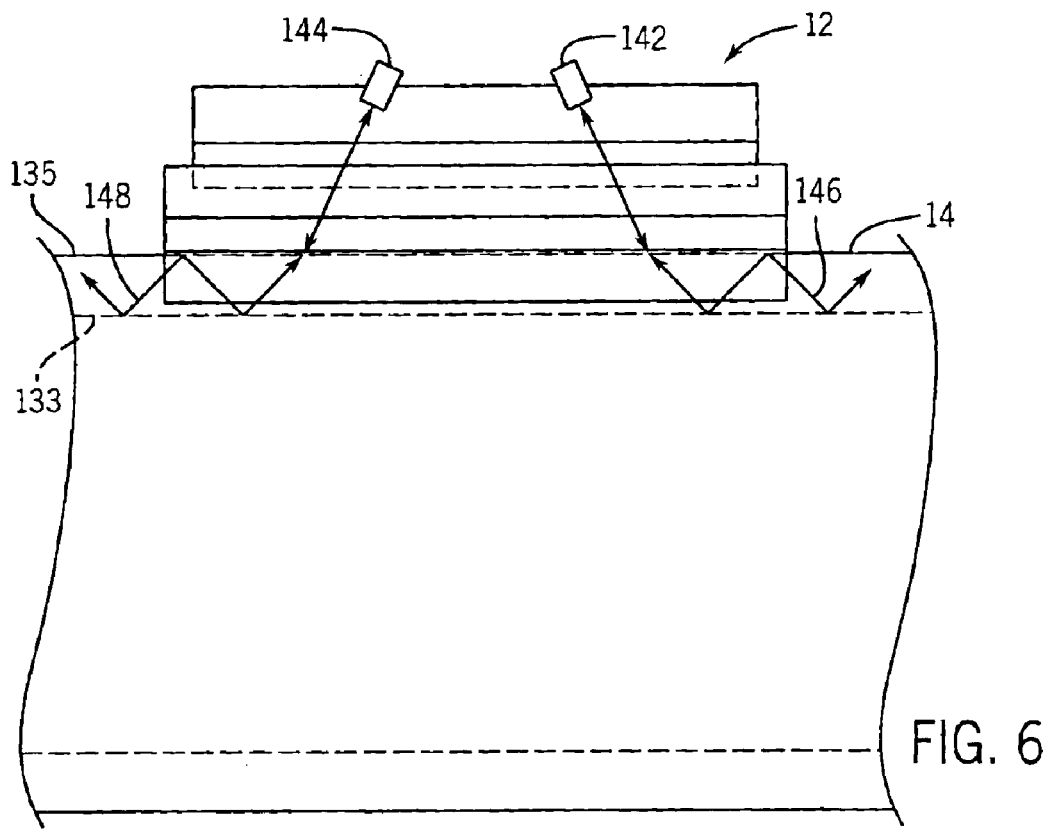
FIG. 6 is a side view of the ultrasonic test assembly of FIG. 2 top-mounted to the tubular good illustrating longitudinal ultrasonic testing in opposite directions along the longitudinal axis of the tubular good.

FIGS. 5 and 6 illustrate sound wave transmission through the tubular good 14 between inner and outer surfaces 133 and 135 in multiple directions oriented to detect transverse and longitudinal flaws, respectively. FIG. 5 is an end view of the ultrasonic test assembly 12 top-mounted to the tubular good 14 illustrating the operation of transversely-oriented ultrasonic transducer units 134 and 136, which are disposed in the transducer mount panels 34 and 36, respectively. As illustrated, the transversely-oriented ultrasonic transducer units 134 and 136 transmit ultrasounds 138 and 140 through fluid in the fluid chamber 30 at the appropriate incident angle, into the tubular good 14 at an angle of approximately 45 degrees, and around the circumference of the tubular good 14 in clockwise and counterclockwise directions, respectively. Again, the ultrasounds 138 and 140 may be spot-focused or line-focused by using spherical or cylindrical lenses, respectively. Moreover, the direct fluid interface between the ultrasonic transducer units 134 and 136 and the tubular good 14 provides greater sensitivity and less signal degradation than a solid interface. If a longitudinal flaw exists in the tubular good 14, then the respective ultrasound 138 or 140 reflects back to the respective ultrasonic transducer unit 134 or 136. The respective ultrasonic transducer unit 134 or 136 then converts the reflected sound (or echo) into electrical energy, which is used to identify the longitudinal flaw to the ultrasonic test control system 11 illustrated by FIG. 2.

FIG. 6 is a side view of the ultrasonic test assembly 12 top-mounted to the tubular good 14 illustrating the operation of longitudinally-oriented ultrasonic transducer units 142 and 144, which are disposed in the transducer mount panels 34 and 36. As illustrated, the longitudinally-oriented ultrasonic transducer units 142 and 144 transmit ultrasounds 146 and 148 through fluid in the fluid chamber 30 at the appropriate incident angle, into the tubular good 14 at an angle of 45 degrees, and longitudinally along the tubular good 14 in rightward and leftward directions, respectively. As discussed above, the present technique improves the sensitivity and reduces signal degradation of the ultrasonic transducer units 142 and 144 by using a direct fluid interface and curved lenses for the transmission of ultrasounds 138 and 140. If a transverse flaw exists in the tubular good 14 in either the leftward or rightward direction, then the respective ultrasound 146 or 148 reflects back to the respective ultrasonic transducer unit 142 or 144. The respective ultrasonic transducer unit 142 or 144 then converts the reflected sound (or echo) into electrical energy, which is used to identify the transverse flaw to the ultrasonic test control system 11 illustrated by FIG. 2.

Figure 7:
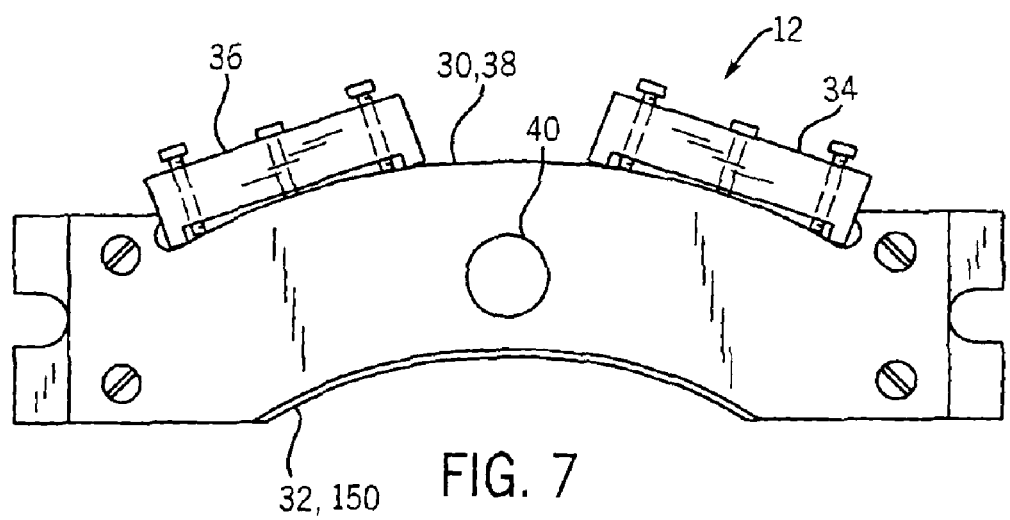
FIGS. 7 and 8 are side and bottom views of the ultrasonic test assembly of FIG. 2 illustrating a removable contact member disposed on an interface structure of the ultrasonic test assembly.
Figure 8:
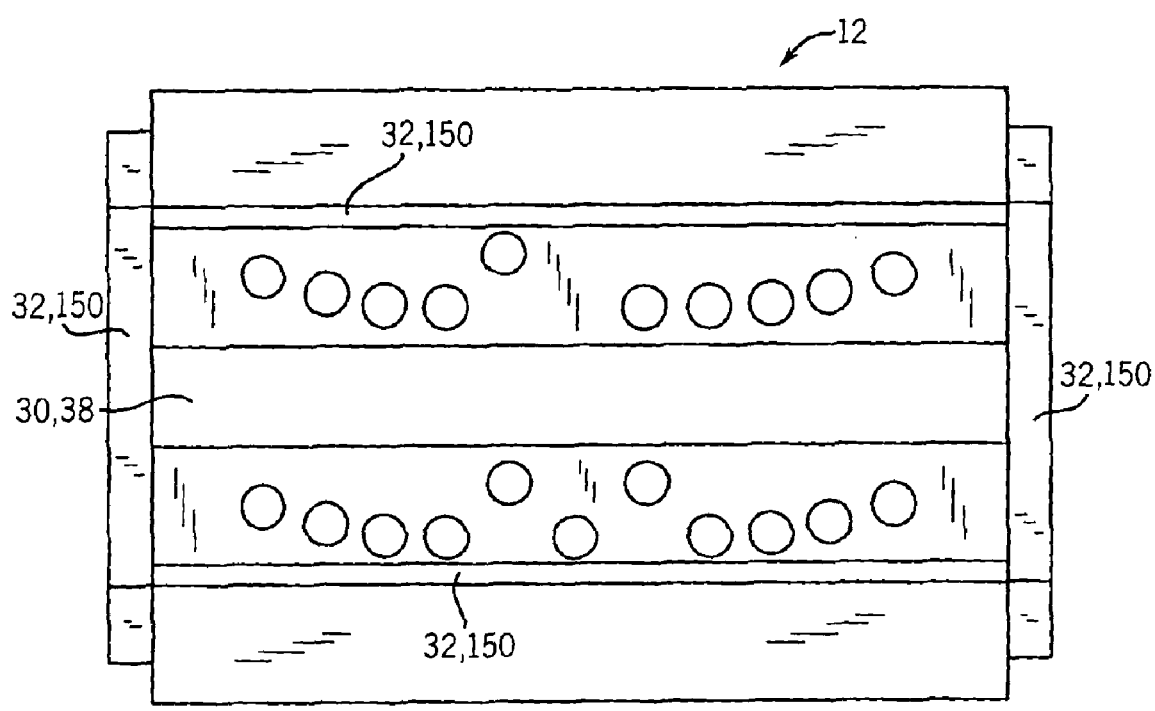

In addition to the fluid interface and curved lenses of the ultrasonic test assembly 12, the present technique may have a removable seal or gasket for interfacing with the top surface 42 of the tubular good 14. FIGS. 7 and 8 are end and bottom views of the ultrasonic test assembly 12 illustrating an exemplary removable contact member 150, which may comprise any suitable material for movably contacting the tubular good 14. For example, the removable contact member 150 may comprise a low friction or self-lubricating material, such as UHMW, Teflon, or any other suitable long-chain polymer. In operation, the removable contact member 150 slides along the surface of the tubular good 14 and substantially retains fluid within the fluid chamber 30 of the ultrasonic test assembly 12. The removable contact member 150 may survive a relatively large number of ultrasonic tests, such as 200 tests, depending on the surface conditions of the tubular good 14, the thickness and substance of the removable contact member 150, and various other testing conditions. At any time, the removable contact member 150 may be replaced with another removable contact member 150 to refurbish the ultrasonic test assembly 12 or to accommodate a different ultrasonic test, a different tubular good, or any other testing conditions. The removable contact member 150 also allows the ultrasonic test assembly 12 to be formed from any desired material, because the removable contact member 150 interfaces and wears along the tubular good 14 rather than the ultrasonic test assembly 12. For example, the ultrasonic test assembly 12 may comprise aluminum, nylon, nylatride, Delrin, or any other rigid material.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A system for ultrasonically testing a tubular, comprising:
    an ultrasonic test assembly, comprising:
        a carrier unit movably positional along a surface of the tubular between opposite ends of the tubular; and
        an ultrasonic transducer mount unit movably positional along the carrier unit to outer regions of the carrier unit extendable beyond the opposite ends of the tubular.

2. The system of claim 1, wherein the ultrasonic test assembly comprises a fluid chamber formed between the ultrasonic transducer mount unit and a mount interface of the carrier unit.

3. The system of claim 1, wherein the ultrasonic transducer mount unit has a fluid interface between the carrier unit and mount receptacles for ultrasonic transducers in the ultrasonic transducer mount unit.

4. The system of claim 1, wherein the ultrasonic transducer mount unit has a solid interface between the carrier unit and mount receptacles for ultrasonic transducers in the ultrasonic transducer mount unit.

5. The system of claim 1, wherein the ultrasonic test assembly is top-mountable to the tubular.

6. The system of claim 1, wherein the carrier unit comprises a removable interface member, which is movably positional along the surface of the tubular.

7. The system of claim 1, comprising a lengthwise tubular-positioning mechanism coupled to the ultrasonic test assembly.

8. The system of claim 1, comprising a rotational drive coupleable to the tubular.

9. The system of claim 1, comprising a positioning system having a helical test pattern routine.

10. A system for ultrasonically testing a tubular, comprising:
    a top-mountable ultrasonic test assembly, comprising:
        a fluid carrier unit, comprising:
            a central interface portion movably positional along a surface of the tubular between opposite ends of the tubular; and
            outer carrier portions disposed about the central interface portion and positional beyond the respective opposite ends of the tubular, and
        an ultrasonic transducer mount unit movably positional along the fluid carrier unit to the outer carrier portions.

11. The system of claim 10, wherein the ultrasonic transducer mount unit comprises receptacles for a plurality of ultrasonic transducers in different testing orientations.

12. The system of claim 11, wherein the different testing orientations comprises longitudinal, transverse, and oblique testing orientations.

13. The system of claim 10, wherein the ultrasonic transducer mount unit comprises an ultrasonic transducer having a curved lens.

14. The system of claim 10, wherein the ultrasonic transducer mount unit comprises an ultrasonic transducer having a piezoelectric element.

15. The system of claim 10, wherein the central interface has a removable wear member adapted to seal substantially against the surface of the tubular.

16. The system of claim 10, wherein the ultrasonic transducer mount unit is mounted to a linear positioning mechanism extending lengthwise along the fluid carrier unit.

17. A method, comprising the acts of:
    providing a movable tubular interface having a central portion movably positional between opposite ends of the tubular and having outer portions disposed about the central portion and positional beyond the respective opposite ends; and movably coupling an ultrasonic test unit to the movable tubular interface on a corner extendable across the central and outer portions.

18. The method of claim 17, wherein the act of providing the movable tubular interface comprises the act of forming a fluid testing interface with the tubular.

19. The method of claim 17, wherein the act of movably coupling the ultrasonic test unit comprises the act of forming a fluid interface between the movable tubular interface and ultrasonic transducers disposed in the ultrasonic test unit.

20. An ultrasonically tested tubular produced by the process comprising the acts of:

providing a movable tubular interface having a central portion movably positional between opposite ends of the tubular and having outer portions disposed about the central portion and positional beyond the respective opposite ends; and movably coupling an ultrasonic test unit to the movable tubular interface on a corner extendable across the central and outer portions.

* * * * *